United States Patent
Duval

(10) Patent No.: US 9,487,552 B2
(45) Date of Patent: Nov. 8, 2016

(54) METHOD FOR PREPARING AN EXTRACT OF CENTELLA ASIATICA

(75) Inventor: Charles Duval, Eyguieres (FR)

(73) Assignee: NATUREX, S.A., Avignon (FR)

( * ) Notice: Subject to any disclaimer, the term of this patent is extended or adjusted under 35 U.S.C. 154(b) by 188 days.

(21) Appl. No.: 13/821,661

(22) PCT Filed: Sep. 2, 2011

(86) PCT No.: PCT/FR2011/052013
§ 371 (c)(1),
(2), (4) Date: Mar. 8, 2013

(87) PCT Pub. No.: WO2012/032250
PCT Pub. Date: Mar. 15, 2012

(65) Prior Publication Data
US 2013/0172541 A1 Jul. 4, 2013

(30) Foreign Application Priority Data
Sep. 9, 2010 (FR) ..................... 10 57179

(51) Int. Cl.
*C07H 15/24* (2006.01)
*A61K 36/23* (2006.01)

(52) U.S. Cl.
CPC ............. *C07H 15/24* (2013.01); *A61K 36/23* (2013.01); *A61K 2236/331* (2013.01); *A61K 2236/39* (2013.01)

(58) Field of Classification Search
None
See application file for complete search history.

(56) References Cited

U.S. PATENT DOCUMENTS

| | | | |
|---|---|---|---|
| 7,402,669 B2 * | 7/2008 | Loiseau et al. | 536/128 |
| 2009/0131698 A1 * | 5/2009 | Gao et al. | 552/625 |
| 2009/0233876 A1 * | 9/2009 | Auriol et al. | 514/27 |

OTHER PUBLICATIONS

Tung, H. H., Paul, E. L., Midler, M., & McCauley, J. A. (2009). Crystallization of organic compounds: an industrial perspective. John Wiley & Sons.*

Flamini, R. (Ed.). (2008). Hyphenated techniques in grape and wine chemistry. John Wiley.*

Su, W. W., & Humphrey, A. E. (1991). Production of rosmarinic acid from perfusion culture of Anchusa officinalis in a membrane-aerated bioreactor. Biotechnology letters, 13(12), 889-892.*

Jia, G., & Lu, X. (2008). Enrichment and purification of madecassoside and asiaticoside from Centella asiatica extracts with macroporous resins. Journal of Chromatography A, 1193(1), 136-141.*

* cited by examiner

*Primary Examiner* — Shaojia Anna Jiang
*Assistant Examiner* — Dale R Miller
(74) *Attorney, Agent, or Firm* — Matthias Scholl, PC; Matthias Scholl

(57) ABSTRACT

The invention relates to a method for preparing a refined extract of *Centella asiatica* comprising a mixture of madecassoside and terminoloside. The method comprises: passage over adsorbent resin; elution with an eluent comprising at least 30 wt. % of an alcoholic solvent; and a recrystallization step using a mixture of solvents, comprising water and an alcoholic solvent.

15 Claims, No Drawings

METHOD FOR PREPARING AN EXTRACT OF CENTELLA ASIATICA

CROSS-REFERENCE TO RELATED APPLICATIONS

This is a National Stage Application of International Patent Application No. PCT/FR2011/052013, with an international filing date of Sep. 2, 2011, and further claims foreign priority benefits to French Patent Application No. 1057179, filed Sep. 9, 2010.

BACKGROUND OF THE INVENTION

1. Field of the Invention

The present invention relates to a method for preparing an extract of *Centella asiatica* comprising a mixture of madecassoside, terminoloside and asiaticoside.

2. Brief Description of the Related Art

*Centella asiatica* belongs to the Umbelliferae (Apiaceae) family, particularly the Hydrocotyle subfamily. This plant has been known and used by traditional medicines for over 3000 years. It is of particular interest for the healing, sedative, analgesic, antidepressant, antidepressant and antimicrobial properties thereof.

The active compounds of *Centella asiatica* are pentacyclic triterpenes, which are either in the form of triterpene genins: asiatic acid (formula I) and madecassic acid (formula II), or in the form of triterpene heterosides: asiaticoside (formula III), madecassoside (formula IV) and terminoloside (formula V).

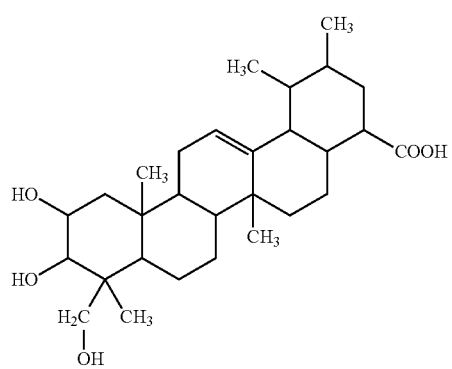

Asiatic acid

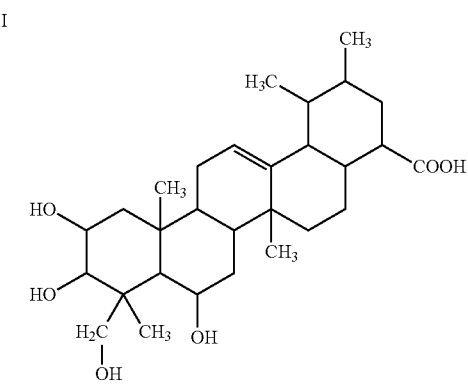

madecassic acid

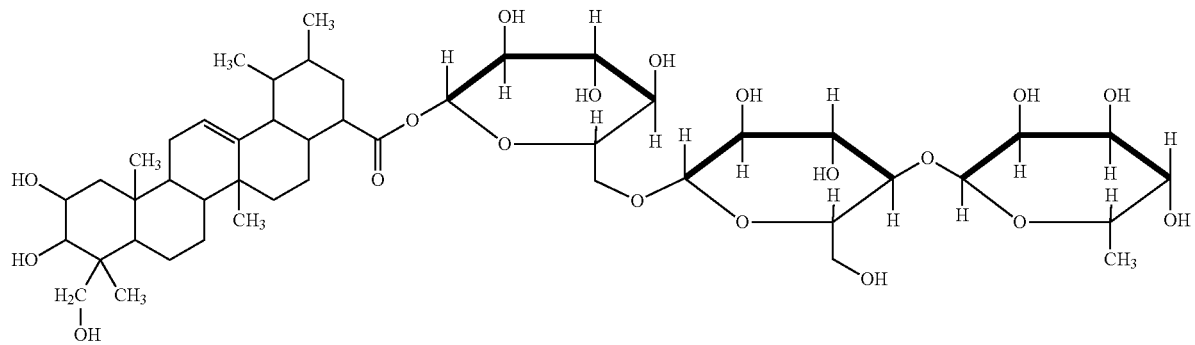

asiaticoside

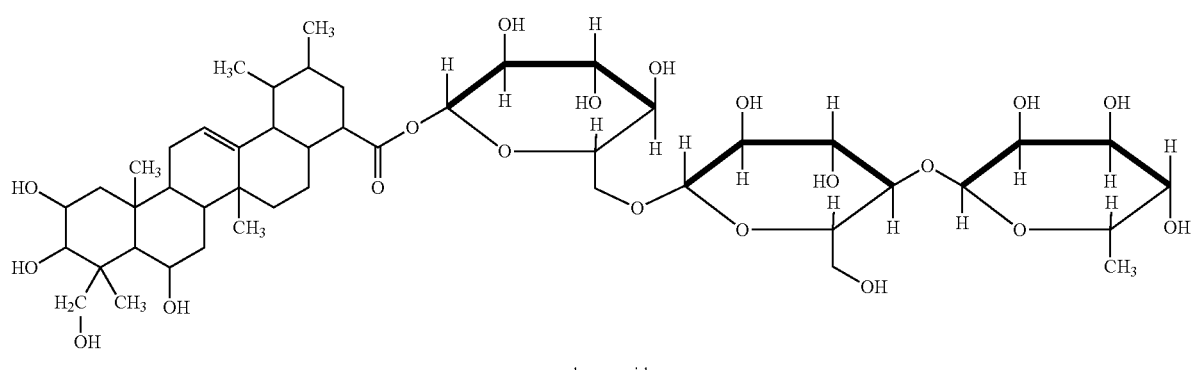

madecassoside

V

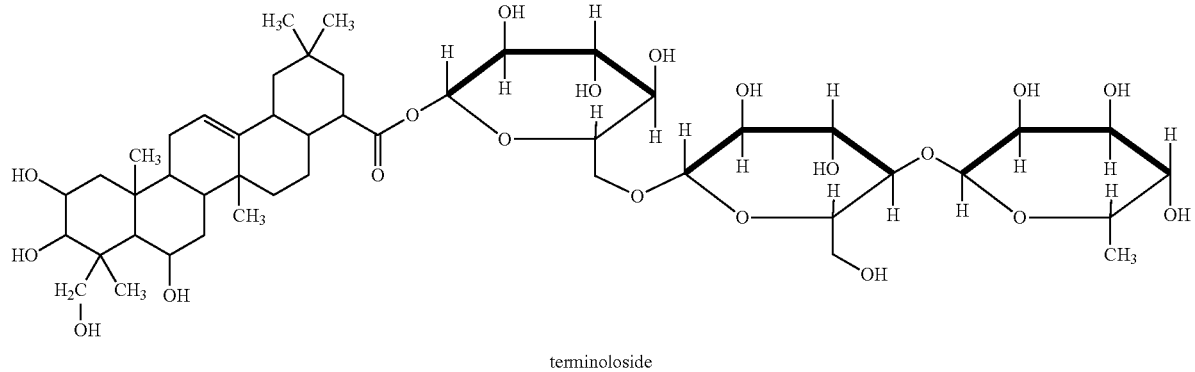

terminoloside

Terminoloside is a position isomer of madecassoside and has the same sugar chain, i.e. a glucose-glucose-rhamnose chain. The structure of the terpene ring of terminoloside is equivalent to that of the terpene ring of terminolic acid.

To the inventors' knowledge, no isomer of asiaticoside has been detected to date. However, it could be assumed that a position isomer of asiaticoside exists, having a similar isomerism to that existing between madecassoside and terminoloside.

The heterosides of Centella asiatica, asiaticoside and madecassoside, are sugar complexes forming the reserve forms of asiatic acid and madecassic acid, respectively, of the plant.

Triterpene molecules are of particular interest due to the collagen synthesis regulating and activating activity thereof. Genins and heterosides extracted from Centella asiatica particularly promote collagen 1 and 3 synthesis. These active substances are used in the pharmaceutical sector essentially for facilitating healing and for treating venous insufficiency. They are used in the cosmetic sector essentially as anti-wrinkle and anti-cellulite agents. The active compounds of Centella asiatica more commonly used in the prior art are asiatic and madecassic acids and asiaticoside.

Since madecassoside is very soluble in water, it is generally carried away in washing water during conventional liposoluble active substance extraction methods.

The international application WO 2004/062678 provides a method for preparing an extract of Centella asiatica comprising a mixture of madecassoside, terminoloside and asiaticoside, said method comprising a step for selective delipidation by liquid/liquid extraction followed by concentration of the hydro-alcoholic phase obtained and successive filtrations, this sequence being intended to remove asiaticoside from the mixture of madecassoside and terminoloside. However, madecassoside solubilizes a portion of the asiaticoside, this residual proportion of asiaticoside needing to be removed by silica gel chromatography, a costly purification technique which is not popular on industrial scales.

DETAILED DESCRIPTION OF THE INVENTION

Surprisingly, the inventors have developed a novel extraction method for preparing an extract of Centella asiatica comprising a mixture of madecassoside, terminoloside and asiaticoside. In this method, the inventors have used a novel step, for purifying a solution comprising a mixture of madecassoside, terminoloside and asiaticoside.

The present invention relates to the use of a passage step over adsorbent resin for preparing an extract of Centella asiatica comprising a mixture of madecassoside, terminoloside and asiaticoside.

The adsorbent resin used in the method according to the invention is advantageously a resin suitable for adsorbing triterpene heterosides contained in Centella asiatica, such as for example styrene-divinylbenzene or formo-phenolic type adsorbent resins.

The present invention also relates to a method for preparing an extract of Centella asiatica comprising a mixture of madecassoside, terminoloside and asiaticoside, said method comprising the following steps:
  α) passage over adsorbent resin of an aqueous solution comprising a mixture of madecassoside, terminoloside and asiaticoside, and
  β) elution of said adsorbent resin with an eluent comprising at least 30% wt. of an alcoholic solvent, optionally water.

Within the scope of the present description, the term "alcoholic solvent" refers to a solvent comprising at least one —OH alcohol function, such as methanol, ethanol, propanol, butanol, ethylene glycol, glycerol, and more specifically methanol and ethanol.

During step α), the passage over adsorbent resin of the solution comprising a mixture of madecassoside, terminoloside and asiaticoside enables the preferential adsorption of these triterpene heterosides.

The eluent used in step β) is optionally an undiluted alcoholic solvent or advantageously a mixture of an alcoholic solvent and water, preferably comprising 50% to 80% alcoholic solvent, preferentially 60% to 70%.

In one advantageous alternative embodiment of the method, step α) is preceded by step a) for extracting the aerial parts of Centella asiatica by means of water or a solvent mixture comprising at least 10% wt. of water, and optionally an alcoholic solvent, whereby an aqueous solution comprising a mixture of madecassoside, terminoloside and asiaticoside is obtained.

Within the scope of the present description, the term "aerial parts of Centella asiatica" refers to Centella asiatica leaves consisting of laminae with not more than 5 cm of petiole.

The active substances are advantageously extracted from the Centella asiatica plant using the aerial parts of the plant, with the primary aim of not damaging the roots thereof and thus enabling the natural renewal of this perennial plant.

In one advantageous alternative embodiment of the method according to the invention, the extraction step comprises a maceration step during which the aerial parts are macerated under stirring, in water or in a solvent mixture, comprising water and optionally an alcoholic solvent.

Within the scope of the present description, a "solvent mixture" particularly refers to a mixture of at least two solvents, preferably two solvents, such as for example water and an alcoholic solvent.

The maceration is advantageously performed using water or a solvent mixture comprising at least 10% wt. of water, and optionally an alcoholic solvent, at a temperature generally between 20 and 90° C., preferably between 50 and 70° C., and preferentially at a temperature in the region of 50° C., for a time generally between 20 and 180 minutes in a [*Centella asiatica*]:[solvent mixture] ratio between 1:2 and 1:20.

The maceration mixture obtained is generally filtered to obtain an aqueous solution comprising a mixture of madecassoside, terminoloside and asiaticoside. This filtration is generally performed by means of successive filtrations, typically with 600 μm, 100 μm and 25 μm porosity filters.

In one alternative embodiment of the method according to the invention, the aqueous solution obtained following the above mentioned extraction step is optionally concentrated, in order to reduce the volumes to be processed and obtain a concentrated solution comprising 2% to 25% dry matter.

The concentrated solution obtained is optionally basified, advantageously by adding a strong mineral base, such as for example an alkaline hydroxide such as lithium hydroxide LiOH, sodium hydroxide NaOH or potassium hydroxide KOH, in solid or aqueous solution form, or quick lime CaO, or slaked lime $Ca(OH)_2$, so as to modify the pH of the concentrated solution to a pH preferably between 8 and 12. The strong mineral base is preferably chosen from NaOH, KOH and CaO.

Adding a strong base generally enables the precipitation, and removal by filtration, of the metals and other substances present liable to react with the strong base. In general, the precipitated or flocculated protein and resinoid compounds are subsequently removed from the basified mixture by filtration.

The filtrate obtained following the filtration step mentioned above can then optionally be acidified, advantageously by adding a strong mineral acid, such as phosphoric acid $H_3PO_4$, hydrochloric acid HCl, nitric acid $HNO_3$, sulfuric acid $H_2SO_4$, perchloric acid $HClO_4$, hydrobromic acid HBr, or an organic acid, such as for example an aromatic or non-aromatic organic compound bearing one or a plurality of —COOH carboxylic acid functions, such as formic acid, ethanoic acid, benzoic acid, citric acid or carbonic acid. This acidification step is suitable for modifying the pH of the filtrate to a pH preferably between 5 and 7. The strong mineral acid is preferably chosen from $H_3PO_4$ and HCl. The organic acid is preferably chosen from citric acid or carbonic acid.

The salts formed and precipitated compounds are generally removed from the acidified mixture by filtration.

In one advantageous alternative embodiment of the method, step β) is followed by the following steps:
 b) passage of the eluate obtained following step β) over discoloring resin, whereby a discolored aqueous phase is obtained, and
 c) vacuum concentration of the discolored aqueous phase, whereby an extract of *Centella asiatica* comprising a mixture of madecassoside, terminoloside and asiaticoside is obtained.

Preferably, the mixture obtained consists of madecassoside, 25% to 65% terminoloside and 20% to 40% asiaticoside.

Preferably, the extract obtained comprises 25% wt. to 65% wt. of a mixture of terminoloside and madecassoside, and 20% to 40% wt. of asiaticoside, in relation to the total weight of the extract.

In one advantageous alternative embodiment of the method according to the invention, the eluate obtained following step β) is first treated with activated carbon. Adding activated carbon generally makes it possible to discolor the eluate, by fixing fatty acids or oxidation products.

This eluate, optionally treated with activated carbon, may then be concentrated by distilling the alcoholic solvent(s). The concentrated eluate is for example then filtered to remove the insoluble compounds in the aqueous phase. A portion of the asiaticoside generally precipitates during the concentration of the eluate and is then generally removed by filtration.

During step b), the eluate obtained in step β), optionally treated with activated carbon, optionally concentrated and filtered, is discolored by passing over discoloring resin, for example a strong anionic styrene-chloride type resin.

In one advantageous alternative embodiment of the method according to the invention, the discolored aqueous phase is then optionally treated by successively passing over a cationic ion exchange resin and over an anionic ion exchange resin, so as to remove dissolved salts and undesirable compounds from the aqueous phase. Advantageously, the cationic resin used is a strong cationic resin having sulfonate type functional groups. Advantageously, the anionic resin used is a strong anionic resin having quaternary ammonium type functional groups. Within the scope of the method according to the invention, the order of the ion exchange resins is important so as to enhance the fixation of residual acid fractions. The order may nonetheless be inverted as required.

The successive passage over cationic and anionic resin may be advantageously repeated, or even carried out by means of a passage of the discolored aqueous phase over a mixed bed of said resins.

During step c), the discolored aqueous phase, optionally treated by passing over cationic and anionic resins, is vacuum-concentrated, and the concentrate obtained is generally vacuum- or spray-dried. The concentration may advantageously be carried out using tangential filtration membrane techniques on an organic or mineral membrane, using media having a cut-off threshold between 200 kDa and 100 kDa (i.e. using molecules having a molecular weight between 200 and 100,000 g/mol).

Following step c), an extract of *Centella asiatica* generally comprising 25% wt. to 65% wt. of a mixture of madecassoside and terminoloside, and 20% wt. to 40% wt. of asiaticoside, in relation to the total weight of the extract, is obtained.

Following step c), an extract of *Centella asiatica* generally comprising 25% to 65% wt. of a mixture of madecassoside and terminoloside, in relation to the total weight of the extract, is obtained.

Following step c), an extract of *Centella asiatica* generally comprising 20% wt. to 40% wt. of asiaticoside, in relation to the total weight of the extract, is obtained.

Within the scope of the present invention, the term "asiaticoside" refers to the chemical molecule according to formula III, optionally in a mixture with any of the oleanic isomers thereof.

The present invention also relates to a method for preparing a refined extract of *Centella asiatica* comprising a mixture of madecassoside, terminoloside and asiaticoside, said method comprising a step for recrystallizing the extract obtained according to the method described above, by means of a solvent mixture comprising water and an alcoholic solvent.

Examples of alcoholic solvents suitable for the recrystallization step include ethanol, methanol and butanol, or a mixture thereof.

Within the scope of the present description, the term "refined extract of *Centella asiatica*" refers to an extract of *Centella asiatica* comprising more than 50% wt. of a mixture of madecassoside and terminoloside, in relation to the total weight of the extract.

Such an extract generally comprises less than 15% wt. of asiaticoside in relation to the total weight of the extract.

The recrystallization step of the method according to the invention is suitable for removing the majority of the asiaticoside and thus increasing the content of the mixture of madecassoside and terminoloside in the refined extract obtained.

The recrystallization purification technique is based on the difference in the hot and cold solubility of compounds in solvents. The solubility of a solid compound generally increases with the temperature. Therefore, when solubilized in a hot solvent, the crystallization thereof may be induced by the cooling of the solution to the supersaturation thereof. Recrystallization thus consists of placing the solid compound to be purified in a solvent or in a solvent mixture, generally at boiling point, and subsequently cooling the solution, inducing the crystallization of the solid, subsequently isolated by filtration. The solute may also be concentrated to precipitation by evaporating the solvent.

More specifically, the recrystallization step comprises the following steps:

d) solubilization of the extract obtained following step c) according to the method described above, in a solvent mixture comprising water and an alcoholic solvent, carried to a temperature between 40° C. and 70° C., whereby a solution is obtained, e) reduction of the temperature of the solution obtained following step d) to a temperature between −20° C. and 30° C., whereby a cooled mixture is obtained, f) filtration of the cooled mixture, whereby a filtrate is obtained, g) concentration of the filtrate, whereby a refined extract of *Centella asiatica* comprising a mixture of madecassoside, terminoloside and asiaticoside is obtained.

Within the scope of the invention, the recrystallization solvent mixture is a solvent mixture comprises water and an alcoholic solved. A particularly advantageous recrystallization solvent mixture comprises 70% water and 30% of an alcoholic solvent, preferably ethanol or methanol, preferably carried to a temperature between 55° C. and 65° C., preferentially in the region of 60° C.

The recrystallization solvent mixture is optionally brought to the boil to enable the solubilization of the extract to be purified.

During the solubilization of the extract obtained following step c), the solvent mixture is generally added drop by drop, so as to be able to stop adding solvent when the entire extract is solubilized.

The solution obtained is then cooled so as to induce the crystallization of the asiaticoside. The reduction in temperature is generally slow and gradual, advantageously over a period of time between 1 and 250 hours, preferably 100 to 250 hours, so as to increase the purity of the asiaticoside crystals formed and thus not trap terminoloside and madecassoside in these crystals, which would lower the content of these compounds in the mother liquor. The temperature of the cooled mixture is generally between −10° C. and 10° C., preferably between −5° C. and 5° C.

The cooled mixture, comprising the crystals formed and the mother liquor particularly comprising terminoloside and madecassoside, is filtered to remove insoluble crystallized and/or precipitated solid compounds at the temperature reached. The crystals removed generally contain over 75% asiaticoside and may be reused.

The filtrate, also referred to as mother liquor, is concentrated by distillation and generally vacuum-dried.

A refined extract of *Centella asiatica*, generally comprising more than 50% wt. of a mixture of madecassoside and terminoloside, or more than 60%, or more than 70%, in relation to the total weight of the extract, is obtained.

This extract further comprises less than 15% wt. of asiaticoside, or less than 10%, in relation to the total weight of the extract.

The present invention also relates to a method for preparing a purified extract of *Centella asiatica* comprising a mixture of madecassoside and terminoloside, said method comprising a step for purifying the refined extract obtained following step g) according to the method described above, by means of a solvent mixture comprising water and an alcoholic solvent.

Within the scope of the present description, the term "purified extract of *Centella asiatica*" refers to an extract of *Centella asiatica* comprising more than 90% wt. of a mixture of madecassoside and terminoloside, in relation to the total weight of the extract. Such an extract generally contains less than 6% wt. of asiaticoside, in relation to the total weight of the extract.

The purification step of the method according to the invention generally makes in possible to remove more than 40%, or more than 50% of the proportion of asiaticoside contained in a refined extract of *Centella asiatica*.

According to a first alternative embodiment of the method according to the invention, the purification step comprises the following steps:

h) addition to the refined extract obtained following step g) according to the method described above, of a solvent mixture comprising an alcoholic solvent, and optionally water, carried to a temperature between 25° C. and 65°, whereby a solution is obtained, i) reduction of the temperature of the solution to a temperature between −20° C. and 30° C., whereby a cooled mixture is obtained, j) filtration of the cooled mixture, whereby a filtrate is obtained, k) concentration of the filtrate, whereby a purified extract of *Centella asiatica* comprising a mixture of madecassoside and terminoloside is obtained.

The solvent mixture added during step h), to a refined extract obtained following step g) according to the method described above, advantageously comprises at least 85% wt. of the alcoholic solvent and preferably at least 95%. This solvent mixture is advantageously carried to a temperature between 30° C. and 50° C., preferentially at a temperature in the region of the 45° C.

During the solubilization of the extract obtained following step g), the solvent mixture is generally added drop by drop, so as to be able to stop adding solvent when the entire extract is solubilized.

The solution obtained is then cooled, generally slowly and gradually, preferably over a period of time between 1 and 250 hours, preferably to a temperature between −15° C. and 15° C., advantageously between −10° C. and 0° C., and preferentially around −5° C.

The cooled mixture, comprising the crystals formed and the mother liquor particularly comprising terminoloside and madecassoside, is filtered to remove insoluble crystallized and/or precipitated solid compounds at the temperature reached. The filtrate, also referred to as mother liquor, is concentrated by distillation and generally vacuum-dried.

Following the purification step of the method according to the invention, a purified extract of *Centella asiatica* generally comprising more than 90% wt. of a mixture of madecassoside and terminoloside, in relation to the total weight of the extract. This extract further comprises less than 6% wt. of asiaticoside in relation to the total weight of the extract.

This purification step may be advantageously repeated two to three times to increase the madecassoside and terminoloside content of the purified extract of *Centella asiatica*. Repeating this purification step makes it possible to attain more than 95% wt., or even more than 98% wt. of a mixture of madecassoside and terminoloside, in relation to the total weight of the extract, and less than 3% wt., or less than 1% wt. of asiaticoside in relation to the total weight of the extract.

The refined extract of *Centella asiatica* obtained following step g) and the purified extract of *Centella asiatica* obtained following step k) may optionally undergo a subsequent purification by means of silica gel preparative chromatography in order to increase the respective madecassoside and terminoloside content thereof. This chromatography step is performed using, as an elution solvent, a solvent mixture comprising an alcoholic solvent and water.

Within the scope of the present description, the eluent used during the preparative chromatography is generally a polar solvent. Advantageously, the solvent is a mixture of water and an alcoholic solvent, such as ethanol, preferably comprising water and ethanol in proportions of 1:1 (50% water and 50% ethanol).

Within the scope of the present invention, the stationary phase used during the preparative chromatography is a non-polar stationary phase. Advantageously, the stationary phase consists of grafted non-polar silicas. The non-polar grafts advantageously have 2 to 18 carbon atoms, and more advantageously 12 to 18 carbon atoms.

The present invention also relates to a method for preparing a purified extract of *Centella asiatica* comprising a mixture of madecassoside and terminoloside, said method comprising the following steps:
a) extraction of the aerial parts of *Centella asiatica* by means of water or a solvent mixture comprising at least 10% wt. of water, and optionally an alcoholic solvent, whereby a solution is obtained,
α) passage over adsorbent resin of the solution,
β) elution of said adsorbent resin with an eluent comprising at least 30% wt. of an alcoholic solvent, and optionally water, whereby an eluate is obtained,
b) passage of the eluate over discoloring resin, whereby a discolored aqueous phase is obtained,
c) concentration of the discolored aqueous phase, whereby an extract is obtained,
d) solubilization of the extract obtained following step c), in a solvent mixture comprising water and an alcoholic solvent, carried to a temperature between 40° C. and 70° C., whereby a solution is obtained,
e) reduction of the temperature of the solution obtained following step d) to a temperature between −20° C. and 30° C., whereby a cooled mixture is obtained,
f) filtration of the cooled mixture, whereby a filtrate is obtained,
g) concentration of the filtrate, whereby a refined extract is obtained,
h) addition to the refined extract obtained following step g) according to the method described above, of a solvent mixture comprising an alcoholic solvent, and optionally water, carried to a temperature between 25° C. and 65°, whereby a solution is obtained,
i) reduction of the temperature of the solution to a temperature between −20° C. and 30° C., whereby a cooled mixture is obtained,
j) filtration of the cooled mixture, whereby a filtrate is obtained, and
k) concentration of the filtrate,
whereby a purified extract of *Centella asiatica* comprising a mixture of madecassoside and terminoloside is obtained.

EXAMPLES

Example 1

Preparation of Raw Extract of *Centella asiatica*

One kilo of *Centella asiatica* leaves (cut leaves) is immersed in 20 liters of water heated to 70° C. The mixture is left to macerate under stirring for 2 hours, and is filtered by successive filtrations on increasing porosity filters (600 μm, followed by 100 μm, followed by 25 μm).

This produces 16.2 liters of a raw liquid extract, comprising 2% dry matter, with a titer of 11.8% wt. of a mixture of madecassoside and terminoloside, and a titer of 10.9% wt. of asiaticoside, in relation to the total dry matter weight.

Preparation of a Semi-Refined Extract of *Centella asiatica*

The raw liquid extract is passed over RES-00820 (Burgundy) type adsorbent resin, and said resin is then eluted with an eluent consisting of 70% ethanol and 30% water vol/vol.

The ethanolic eluate retrieved is passed over RES-01541 (Burgundy) type anionic discoloring resin, and the discolored phase is dealcoholized by distillation and vacuum-concentrated, whereby a discolored aqueous concentrate is obtained. This concentrate is then freeze-dried.

This produces 70 g of a semi-refined extract, with a titer of 47.2% wt. of a mixture of madecassoside and terminoloside, and a titer of 37.4% wt. of asiaticoside, in relation to the total weight of the extract.

Preparation of Refined Extract of *Centella asiatica*

The semi-refined extract is solubilized in a solution comprising 70% water and 30% methanol, carried to a temperature of 60° C. After the extract has been completely solubilized, the temperature of the solution is reduced over a period of 240 hours to a temperature of 5° C. (cryostat followed by storage in a cold store).

The cooled mixture obtained is filtered, and the filtrate is dealcoholized by distillation and vacuum-concentrated, whereby a refined aqueous concentrate is obtained. This concentrate is then freeze-dried.

This produces 45 g of a refined extract, with a titer of 67.2% wt. of a mixture of madecassoside and terminoloside, and a titer of less than 10% wt. (4.5%) of asiaticoside, in relation to the total weight of the extract.

Preparation of Purified Extract of *Centella asiatica*

The refined extract is solubilized in a solution comprising 5% water and 95% methanol, carried to a temperature of 45° C. After the extract has been completely solubilized, the temperature of the solution is reduced over a period of 120 hours to a temperature of 5° C.

The cooled mixture obtained is filtered, and the filtrate is dealcoholized by distillation and vacuum-concentrated, whereby a purified aqueous concentrate is obtained. This concentrate is then freeze-dried.

This produces 20 g of a purified extract, with a titer of more than 90% wt. (91.2%) of a mixture of madecassoside and terminoloside, and a titer of less than 6% wt. (3.1%) of asiaticoside, in relation to the total weight of the extract.

Example 2

Preparation of Raw Extract of *Centella asiatica*

One kilo of *Centella asiatica* leaves (cut leaves) is immersed in 15 liters of 70% vol. ethanol heated to 50° C. The mixture is left to macerate under stirring for 2 hours, and is filtered by successive filtrations on increasing porosity filters (600 μm, followed by 100 μm, followed by 25 μm).

The filtrate is then dealcoholized by distillation and the concentrated filtrate is filtered.

This produces 3.7 liters of a raw liquid extract, comprising 9% dry matter, with a titer of 11.2% wt. of a mixture of madecassoside and terminoloside, and a titer of 8.6% wt. of asiaticoside, in relation to the total dry matter weight.

Preparation of a Semi-Refined Extract of *Centella asiatica*

The raw liquid extract is passed over RES-00408 (Burgundy) type adsorbent resin, and said resin is then eluted with an eluent consisting of 60% ethanol and 40% water vol/vol.

The ethanolic eluate retrieved is then dealcoholized by distillation and is passed over RES-01953 (Burgundy) type anionic discoloring resin, followed by RES-01747 (Burgundy) type cationic ion exchange resin, followed by RES-02056 (Burgundy) type anionic ion exchange resin. The discolored and deionized phase obtained is vacuum-concentrated, whereby a discolored and deionized aqueous concentrate is obtained. This concentrate is then freeze-dried (optionally replaced by spray-drying).

This produces 60 g of a semi-refined extract, with a titer of 47.2% wt. of a mixture of madecassoside and terminoloside, and a titer of 27.4% wt. of asiaticoside, in relation to the total weight of the extract.

Preparation of Refined Extract of *Centella asiatica*

The semi-refined extract is solubilized in a solution comprising 70% water and 30% methanol, carried to a temperature of 60° C. After the extract has been completely solubilized, the temperature of the solution is reduced over a period of 240 hours to a temperature of 5° C. (cryostat followed by storage in a cold store).

The cooled mixture obtained is filtered, and the filtrate is dealcoholized by distillation and vacuum-concentrated, whereby a refined aqueous concentrate is obtained. This concentrate is then freeze-dried.

This produces 35 g of a refined extract, with a titer of 67.5% wt. of a mixture of madecassoside and terminoloside, and a titer of 13.2% wt. of asiaticoside, in relation to the total weight of the extract.

Preparation of Purified Extract of *Centella asiatica*

The refined extract is solubilized in a solution comprising 5% water and 95% methanol, carried to a temperature of 45° C. After the extract has been completely solubilized, the temperature of the solution is reduced over a period of 120 hours to a temperature of 5° C.

The cooled mixture obtained is filtered, and the filtrate is dealcoholized by distillation and vacuum-concentrated, whereby a purified aqueous concentrate is obtained. This concentrate is then freeze-dried.

This produces 20 g of a purified extract, with a titer of more than 90% wt. (91.5%) of a mixture of madecassoside and terminoloside, and a titer of less than 6% wt. (4.6%) of asiaticoside, in relation to the total weight of the extract.

The invention claimed is:

1. A method for preparing a refined extract of *Centella asiatica* comprising more than 50% wt. of a mixture of madecassoside and terminoloside in relation to the total weight of the extract, said method comprising the following steps:
   a. maceration under stirring of the aerial parts of leaves of the *Centella asiatica* plant in water or in a solvent mixture, comprising at least water and optionally an alcoholic solvent, at a temperature of 20 to 90° C. and for between 20 and 180 minutes, wherein a ratio of *Centella asiatica* to the solvent mixture is between 1:2 and 1:20, followed by filtration of the maceration mixture, whereby an aqueous solution is obtained;
      α. passage of the aqueous solution obtained over an adsorbent resin to adsorb triterpene heterosides, wherein said adsorbent resin is styrene-divinylbenzene or phenol formaldehyde resin;
      β. elution of said triterpene heterosides from said adsorbent resin with an eluent comprising at least 30% wt. of an alcoholic solvent and optionally water, whereby an eluate is obtained, followed by:
   treatment of the eluate obtained with activated carbon;
   b. passage of the treated eluate over a strong anionic styrene-chloride type discoloring resin followed by treatment by means of successive passage(s) over a strong cationic ion exchange resin comprising sulfonate type functional groups, and over a strong anionic ion resin comprising quaternary ammonium type functional groups, or passage of the eluate over said mixed resins, whereby a discolored aqueous phase is obtained;
   c. vacuum-concentration of the discolored aqueous phase using tangential filtration membrane techniques on an organic or mineral membrane, using media having a cut-off threshold between 200 kDa and 100 kDa, whereby an extract is obtained, followed by recrystallization of the extract obtained by:
   d. solubilization of the extract obtained in a solvent mixture comprising 70 vol. % water and 30 vol. % methanol, carried to a temperature between 55° C. and 65° C., whereby a solution is obtained;

e. reduction of the temperature over a period from 100 to 250 hours to a cooled mixture temperature between −10° C. and 10° C., whereby a cooled mixture is obtained;

f. filtration of the cooled mixture, whereby a filtrate is obtained; and g. concentration of the filtrate by distillation, whereby a refined extract comprising less than 15% wt. of asiaticoside in relation to the total weight of the extract is obtained.

2. The method of claim 1, wherein the solvent mixture in step a) is a mixture of at least two solvents comprising at least 10% wt. of water and an alcoholic solvent.

3. The method of claim 1 wherein the aerial parts of *Centella asiatica* are macerated at a temperature between 50° C. and 70° C.

4. The method of claim 1 wherein the aerial parts of *Centella asiatica* are macerated at a temperature of 50° C.

5. The method of claim 1, wherein the maceration mixture is filtered by means of successive filtrations with 600 pm, 100 pm and 25 pm porosity filters.

6. The method of claim 1, wherein step a) is preceded by the following steps:
  (a)(i) concentration of the filtrate obtained following step a); followed by
  (a)(ii) basification with a strong alkaline hydroxide mineral base (lithium hydroxide LiOH, sodium hydroxide NaOH or potassium hydroxide KOH) in solid or aqueous solution form, or quick lime CaO, or slaked lime Ca(OH)2; followed by
  (a)(iii) acidification with a strong mineral acid such as phosphoric acid H3PO4, hydrochloric acid HC1, nitric acid HNO3, sulphuric acid H2SO4, perchloric acid HClO4, hydrobromic acid HBr, or organic acid; and
  (a)(iv) filtration of the acidified mixture.

7. The method of claim 1, wherein the eluent in step β comprises 60 to 70% wt. of an alcoholic solvent, and more specifically 60 to 70% ethanol, and water.

8. The method of claim 1, wherein step b) is preceded by the following steps:
  (b)(i) concentration of the eluate obtained by distilling the alcoholic solvent(s); and
  (b)(ii) filtration of the distilled eluate.

9. The method of claim 1, wherein step d) is preceded by a vacuum- or spray-drying step.

10. The method of claim 1, wherein the solvent mixture added in step d) is carried to a temperature in the region of 60° C.

11. The method of claim 1, wherein the temperature is reduced in step e) to a cooled mixture temperature between −5° C. and 5° C.

12. A method for preparing a purified extract of *Centella asiatica* comprising more than 90% wt. of a mixture of madecassoside and terminoloside in relation to the total weight of the extract, the method comprising a step for purifying the refined extract obtained of the method of claim 1, said purification step comprising the following steps:
  h. addition to refined extract obtained of the method of claim 1 of a solvent mixture comprising at least 85% wt. of methanol and water, carried to a temperature between 30° C. and 50°, whereby a solution is obtained;
  i. reduction of the temperature of the solution over a period from 1 to 250 hours to a temperature between −15° C. and 15° C., whereby a cooled mixture is obtained;
  j. filtration of the cooled mixture whereby a filtrate is obtained; and
  k. concentration by distillation of the filtrate, whereby a purified extract comprising less than 6%, or less than 1% wt. of asiaticoside in relation to the total weight of the extract is obtained.

13. The method of claim 12, wherein the solvent mixture in step h) is carried to a temperature of 45° C.

14. The method of claim 12, wherein the temperature is reduced in step i) over a period from 100 to 250 hours to a cooled mixture temperature of about −5° C.

15. The method of claim 1, wherein said adsorbent resin is phenol formaldehyde resin.

* * * * *

UNITED STATES PATENT AND TRADEMARK OFFICE
CERTIFICATE OF CORRECTION

PATENT NO. : 9,487,552 B2
APPLICATION NO. : 13/821661
DATED : November 8, 2016
INVENTOR(S) : Charles Duval Page 1 of 1

It is certified that error appears in the above-identified patent and that said Letters Patent is hereby corrected as shown below:

In the Claims

In Column 13, Lines 20-21, in Claim 5, delete "600 pm, 100 pm and 25 pm" and insert -- 600 µm, 100 µm and 25 µm --, therefor;

In Column 13, Line 22, in Claim 6, delete "step a)" and insert -- step α) --, therefor;

In Column 13, Line 24, in Claim 6, delete "(a)(i)" and insert -- (α)(i) --, therefor;

In Column 13, Line 26, in Claim 6, delete "(a)(ii)" and insert -- (α)(ii) --, therefor;

In Column 13, Line 31, in Claim 6, delete "(a)(iii)" and insert -- (α)(iii) --, therefor;

In Column 13, Line 35, in Claim 6, delete "(a)(iv)" and insert -- (α)(iv) --, therefor.

Signed and Sealed this
Twenty-eighth Day of March, 2017

Michelle K. Lee
*Director of the United States Patent and Trademark Office*